US005918620A

United States Patent [19]

Rauber

[11] Patent Number: 5,918,620

[45] Date of Patent: Jul. 6, 1999

[54] PRESSURIZED AND SEALING DEVICE AND A PROCESS FOR HERMETIC SYSTEMS

[75] Inventor: Diego Luiz Rauber, Joinville-SC, Brazil

[73] Assignee: Empresa Brasileira De Compressores S./A-Embraco, Joinville-SC, Brazil

[21] Appl. No.: 08/981,838

[22] PCT Filed: Jun. 20, 1997

[86] PCT No.: PCT/BR97/00031

§ 371 Date: Feb. 19, 1998

§ 102(e) Date: Feb. 19, 1998

[87] PCT Pub. No.: WO97/48944

PCT Pub. Date: Dec. 24, 1997

[30] Foreign Application Priority Data

Jun. 20, 1996 [BR] Brazil .................................... 9601861

[51] Int. Cl.[6] ..................................................... A61M 5/00

[52] U.S. Cl. ............................ 137/15; 251/148; 141/383; 285/310

[58] Field of Search ........................ 141/383, 18; 53/471; 137/15; 251/148, 144; 285/310

[56] References Cited

U.S. PATENT DOCUMENTS

| | | | |
|---|---|---|---|
| 2,631,001 | 3/1953 | Griswold | 251/148 |
| 2,640,492 | 6/1953 | Sawicki | 251/148 |
| 3,785,404 | 1/1974 | Gappisch et al. | 251/148 |
| 3,817,302 | 6/1974 | Kowal et al. | 141/383 |
| 5,045,081 | 9/1991 | Dysarz | 141/383 |

FOREIGN PATENT DOCUMENTS

| | | |
|---|---|---|
| 33 07 245 | 9/1984 | Germany . |
| 43 38 722 | 11/1994 | Germany . |
| 1 108 144 | 4/1968 | United Kingdom . |

*Primary Examiner*—A. Michael Chambers
*Attorney, Agent, or Firm*—Darby & Darby

[57] ABSTRACT

Patent of invention for pressurizing and sealing device and process for hermetic systems, provided with a gas feeding conduit (1), comprising: a tubular body (10) defining an internal chamber (13) between a first end (11) which can be tightly seated against an open external end (2) of the gas feeding conduit (1) and a second open end (12), and a pressurized gas inlet nozzle (14) opened into the internal chamber (13); an elastomeric plug (30) which can be positioned inside the tubular body (10) in such a way that it can be selectively displaced from a pressurizing condition, sealing the second end (12) of the tubular body (10) when the internal chamber (13) and the hermetic system are pressurized through the pressurized gas inlet nozzle (14), to a plugging condition, in which it is sealingly fitted and maintained in the external end (2) of the gas feeding conduit (1) after said pressurization has ended; and an impelling means (40), which is coupled to the tubular body (10) and which can be selectively activated through the second end (12) of said body so as to conduct the elastomeric plug (30) from the pressurizing condition to the plugging condition.

13 Claims, 2 Drawing Sheets

PRESSURIZED AND SEALING DEVICE AND A PROCESS FOR HERMETIC SYSTEMS

TECHNICAL FIELD

The present invention refers to a pressurizing and sealing device and process for hermetic systems, particularly used for supplying gases to hermetic compressors for cooling systems of the type used in refrigerators, freezers and air-conditioners, for example.

BACKGROUND OF THE INVENTION

The hermetic compressors for these cooling systems have their shells defining a hermetic chamber to be pressurized by an inert gas, such as nitrogen, and plugged in such a way as to prevent humidity from entering and consequently rusting the components located inside the hermetic chamber during the transport and warehousing of these compressors. Said pressurization is carried out through a gas feeding conduit, generally of a short length, attached to the hermetic shell so as to allow fluid communication between the interior and exterior of the chamber.

Before the inert gas is introduced into the interior of the hermetic shell, an open and of the gas feeding conduit is sealingly closed with an elastomeric element in the form of a plug, which is fitted under pressure and which is later perforated with a reduced diameter needle used to inject gas through the gas feeding conduit.

Although the needles have a small diameter, after they are removed at the end of the pressurizing operation of the shell, the plug remains with its structure broken, allowing the occurrence of small leaks of the gas introduced into the shell (close to 50 PPM). Besides this deficiency, this process of introducing gas into hermetic systems has the disadvantage of being a manual process, thus slow and subject to error.

DISCLOSURE OF THE INVENTION

Thus, it is an object of the present invention to provide a pressurizing and sealing device and process for hermetic systems, such as the hermetic shell of a cooling system compressor, which eliminates the occurrence of leaks which exist in the current technique and which will allow the automation of gas feeding in such systems.

This and other objectives are attained by means of a pressurizing and sealing device for hermetic systems, which is provided with a gas feeding conduit having an open external end comprising: a tubular body defining an internal chamber between a first end which can be tightly seated against the external end of the gas feeding conduit, and a second open end and a pressurized gas inlet nozzle which opens into the internal chamber; an elastomeric plug which can be positioned inside the tubular body in such a way as to be selectively displaceable from a pressurizing condition, sealingly closing the second end of the tubular body when the internal chamber and hermetic system are pressurized through the pressurized gas inlet nozzle, to a plugging condition in which it is sealingly fitted and retained in the external end of the gas feeding conduit after said pressurization has ended; and an impelling means which is coupled to the tubular body and which can be selectively activated through the second end of said body, so as to conduct the elastomeric plug from the pressurizing condition to the plugging condition.

According to the present invention, the pressurizing and sealing process comprises the steps of: a—tightly seating the first end of a tubular body against the open external end of the gas feeding conduit; b—closing a second end of the tubular body with an elastomeric plug; c—pressurizing an internal chamber, defined between the first and second ends of the tubular body; d—selectively displacing the elastomeric plug from the pressurizing condition, in which it closes the second end of the tubular body, to a plugging condition, in which it is sealingly fitted and retained in the open external end of the gas feeding conduit after the pressurization of said internal chamber has ended; and e—separating the first end of the tubular body from the tight seating condition at the end of the gas feeding conduit.

As it can be observed, the invention permits obtaining mechanical pressurizing and plugging conditions for said hermetic systems, without modifying or altering the original hermetic structure of the elastomeric plugs with the use of gas injection needles.

BRIEF DESCRIPTION OF THE DRAWINGS

The invention will be described below, based on the attached drawings, in which.

BEST MODE FOR CARRYING OUT THE INVENTION

Figure 1:
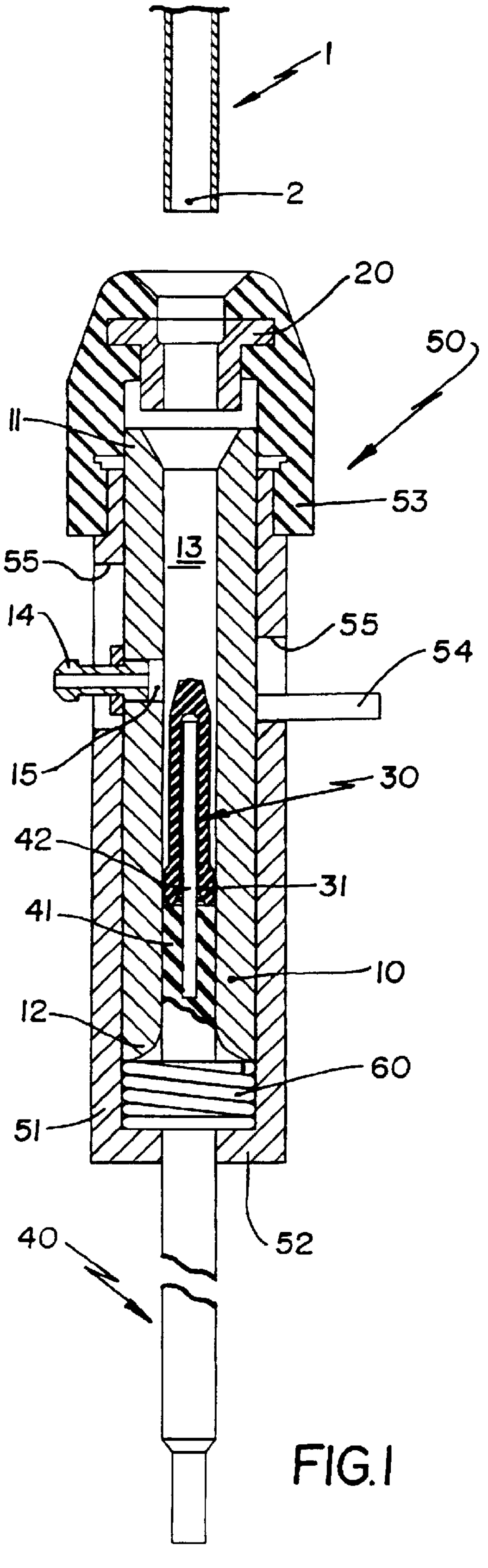
FIG. 1 schematically illustrates a longitudinal vertical cross-section viey of a construction of the gas pressurizing and sealing device for hermetic systems, obtained according to the present invention, in an inoperative condition before being mounted onto a gas feeding conduit.
Figure 2:
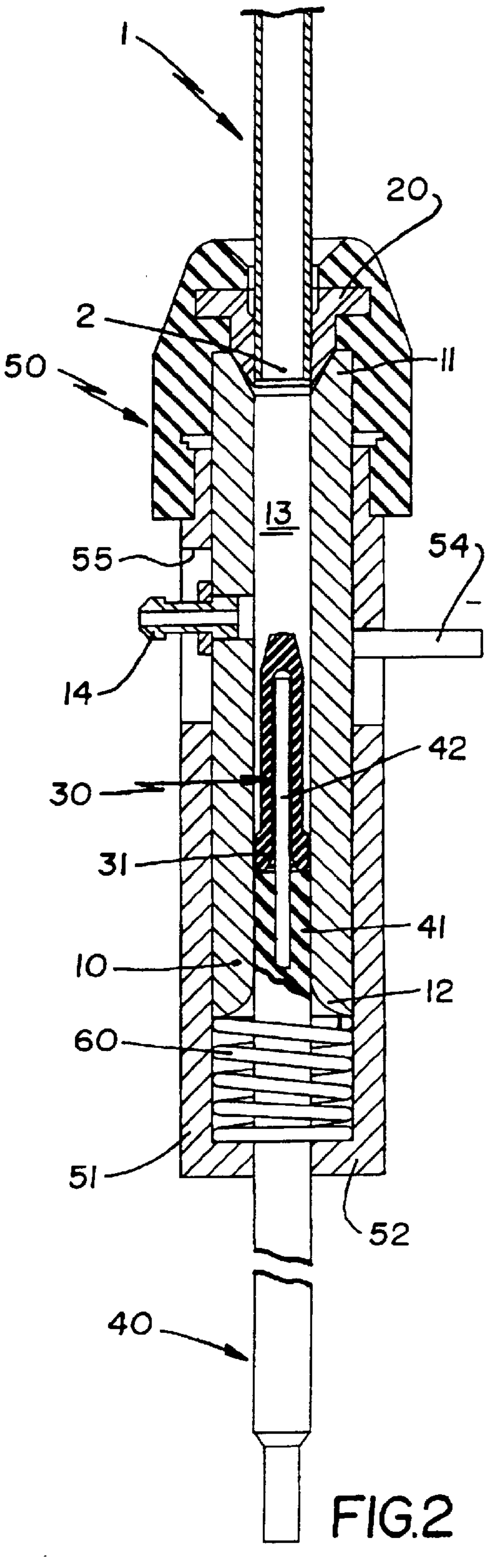
FIG. 2 schematically illustrates the construction of FIG. 1, showing the device of the present invention mounted to the gas feeding conduit to obtain the pressurization of said device.
Figure 4:
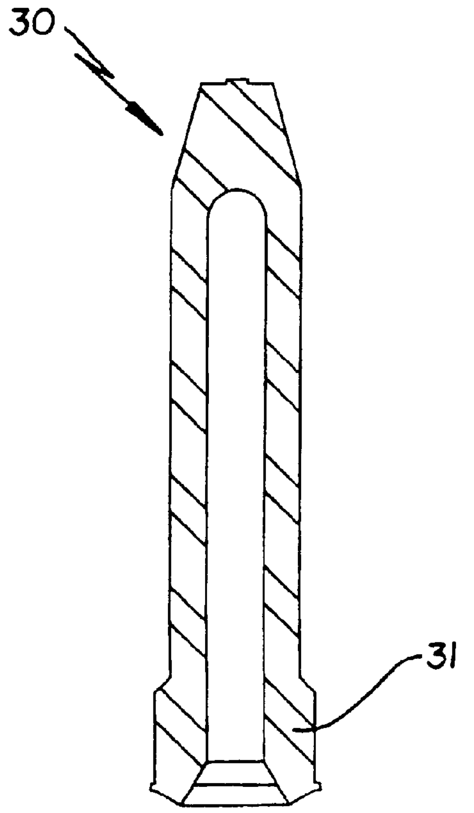
FIG. 4 schematically illustrates a longitudinal cross-section view of the elastomeric plug construction used for sealing the hermetic system when it is pressurized.
Figure 3:
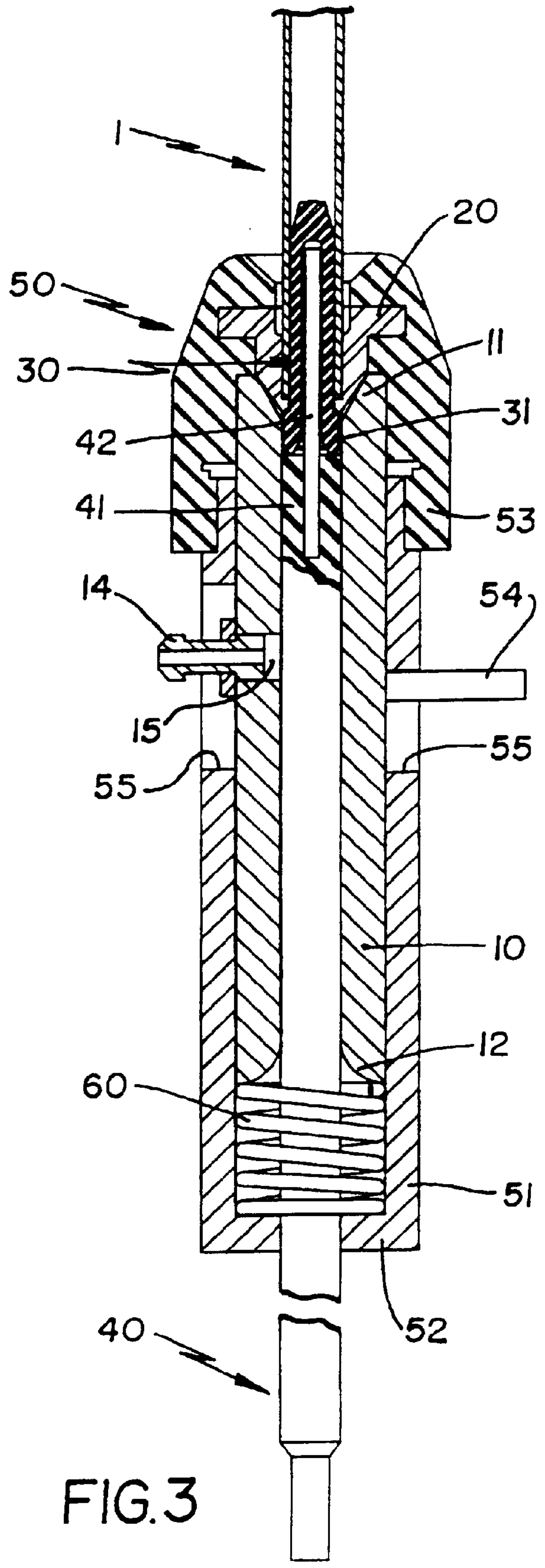
FIG. 3 schematically illustrates the construction of FIG. 2, showing the device of the present invention mounted to the gas feeding conduit after obtaining the pressurization of said device.

The pressurizing and sealing device and process for hermetic systems of the present invention will be described regarding the introduction of a specific volume of inert gas into a hermetic shell of a cooling system compressor, to prevent humidity from entering into said hermetic shell.

The feeding of the inert gas into the hermetic shell occurs by introducing the gas through the low pressure side of the system to which said chamber is connected normally through a gas feeding conduit 1, which is a derivation of a gas circulation pipeline of said system, or still directly into the hermetic chamber.

According to the figures presented, the pressurizing and sealing device of the present invention comprises a cylindrical tubular body 10 having a first end, which is open and which can be tightly seated on an open external end 2 of the gas feeding conduit 1, and at least a second end 12 opposite to the first end 11, axially aligned to it such that, when said tubular body 10 is mounted to the gas feeding conduit 1, said first and second ends 11 and 12 are axially aligned with the external end 2 of the gas feeding conduit 1. The tight seating of the tubular body 10 to the external end 2 is obtained through the elastic deformation of at least part of an annular seal 20, positioned around said external end 2 and which squeezes the latter when the first end 11 of the tubular body 10 is seated thereon. The positioning of the annular seal 20 around the external end 2 occurs in such a way that an end portion of said annular seal 20 remains projecting itself beyond said external end 2 and against which is seated the first end 11 of the tubular body 10. This condition of elastic deformation of the annular seal 20 by the tubular body 10 defines an operational position for the latter. The elastic deformation leads the annular seal 20 to an operational condition of compressing the external end 2 of the feeding conduit 1. During the elastic deformation, the end portion of the annular seal 20, against which is seated the first end 11 of the tubular body, radially compresses the external end 2 while being axially projected towards a lowered portion, in the shape of a wedge for example, of said first end 11 of the tubular body 10, compressively surrounding said external end 2 and sealing the contact between the interior of an internal chamber 13 defined between the first and second ends 11 and 12 of the tubular body 10 and the exterior of the device in question.

After the tubular body 10 has been seated onto the external end 2, an elastomeric plug 30 is positioned inside said tubular body 10 adjacent to the second end 12 of said body, so as to be selectively displaced from a pressurizing condition, sealingly closing said second end 12 into a plugging condition in which it is sealingly fitted and retained in the external end 2 of the gas feeding conduit 1. The displacement of the elastomeric plug 30 to the plugging condition is obtained by means of an impelling means 40 coupled to the tubular body 10 and selectively activated through its second end 12, said impelling means 40 being, for example, an insertion rod provided through the second end 12 of the tubular body 10 and which carries, in an internal end 41 located in the inside of the tubular body 10, a pin 42 to which is coupled the elastomeric plug 30. This coupling occurs by fitting the pin 42 into a tubular base portion 31 of the elastomeric plug 30 facing the second end 12 of the tubular body 10. This fitting occurs, for example, before introducing the elastomeric plug into the tubular body 10 and is maintained until said elastomeric plug 30 reaches its plugging condition. Due to the construction of the elastomeric plug 30, in the plugging condition, its base portion 31 remains external to said external end 2.

Although only one construction for a impelling means 40 has been described, others are possible, without altering the concept presented herein, such as said impelling means being a pressurizing element.

According to the present invention, when the elastomeric plug 30 is in its pressurizing condition, gas which is to be pressurized into the feeding conduit 1 and consequently into the hermetic system is introduced into the internal chamber 13 through a pressurized gas inlet nozzle 14 provided in a substantially radial groove 15 which is defined at a portion of the lateral surface of the tubular body 10 between the first and second ends 11, 12 of the body and opened into the internal chamber 13.

In a preferred and illustrated constructive form, the annular seal 20 is carried by a positioning element 50 which leads said annular seal 20 to the position around the external end 2. Although not shown, said annular seal 20 can be carried by the tubular body 10 itself, which would position it around the external end 2 before provoking the elastic deformation of said seal previously described.

In the construction illustrated, the positioning element 50 is selectively displaced between an inoperative position, in which the annular seal 20 is separated from the external end 2 of the feeding conduit 1, and an operative position for positioning said annular seal 20 around the external end 2 obtained prior to the displacement of the tubular body 10 from an inoperative position, in which its first end 11 is separated from the annular seal 20 which is already positioned around said external end 2, to the operative position, elastically deforming the annular seal 20. The operative position of the tubular body 10 is maintained by a compressing element 60, which is provided between the second end 12 of the tubular body 10 and the positioning element 50 and which acts against said tubular body 10. The inoperative position of the latter is maintained by its action against the compressing element 60 which in this construction is a helicoidal spring.

According to the present invention, the positioning element 50 defines an external guide which displaces the tubular body 10 between its inoperative and operative positions and takes the form of, for example, a continuous tubular cover 51 which internally houses the compressing element 60 adjacent to an annular bottom wall portion 52. The placement of the insertion rod 40 inside the tubular body 10 occurs through this annular bottom wall portion 52.

In the construction illustrated, the tubular cover 51 carries a mandrel element 53, which is threadably affixed to a fastening end of the tubular cover 51 opposite to the annular bottom wall portion 52 and adjacent to the first end 11 of the tubular body 10. The annular seal 20 is located inside the mandrel element 53, adjacent to one of its ends which fits into the external end 2 when the tubular cover 51 is mounted to the latter. For this mounting to occur, the tubular body 10 is led to its inoperative position, when its first end 11 is maintained separated from the fixation end of the tubular cover 51 by means of a lever 54 coupled to the tubular body 10 and which is projected beyond said tubular cover 51. The lever 54 also leads said tubular body 10 into its operative position, preferably retaining it in each of its said inoperative and operative positions.

In the construction illustrated, the tubular cover 51 has lateral openings 55, said openings being defined so as to allow the respective mounting of the pressurized gas inlet nozzle 14 and the lever 54 onto the tubular body 10. In a constructive option, the lateral opening 55 defines a stop for the lever 54, limiting the displacement of the tubular body 10 between its inoperative and operative positions.

Although only one construction of a tubular body 10 has been illustrated, other constructions are possible, such as a tubular body of a shape other than cylindrical, having a plurality of ends interconnected by the internal chamber and having at least one gas feeding nozzle with a respective end opened to said internal chamber, with each said nozzle being in the form of a conduit.

The mounting of the pressurizing and sealing device of the present invention occurs according to a process generically including the following steps: tightly seating the first end 11 of the tubular body 10 against the open end 2 of the gas feeding conduit; closing the second end 12 of the tubular body 10 with the elastomeric plug 30; pressurizing the internal chamber 13 of the tubular body 10; selectively displacing the elastomeric plug 30, from the closing condition of the second end 12 of the tubular body 10 to the plugging condition at the external end 2 of the gas feeding conduit 1, after the pressurization of the gas in the gas feeding conduit 1 has ended; and separating the first end 11 of the tubular body 10, preventing it from being tightly seated onto the external end 2 of the gas feeding conduit 1. The steps previous to the one of pressurizing the internal chamber 13 can occur according to a different sequence than the one presented, without altering the result intended. The process being described also includes, previous to the first step cited, the following steps: positioning the annular seal 20 around the external end 2 of the gas feeding conduit 1; and displacing the tubular body 10 from its inoperative position to its operative position.

I claim:

1. Pressurizing and sealing process for hermetic systems, provided with a gas feeding conduit (1) having an open external end (2), characterized in that it comprises the steps of:

a—tightly seating the first end (11) of a tubular body against the open end (2) of the gas feeding conduit (1);

b—closing a second end (12) of the tubular body (10) with an elastomeric plug (30);

c—pressurizing an internal chamber (13) defined between the first (11) and second (12) ends of the tubular body (10) to introduce the gas into the hermetic system through the gas feeding conduit (1);

d—selectively displacing the elastomeric plug (30) from a pressurizing condition, tightly closing the second end (12) of the tubular body (10), to a plugging condition, tightly fitting it into the external end (2) of the gas feeding conduit (1) once said pressurization has ended; and e—separating the first end (11) of the tubular body (10) from the tight seating condition in relation to the external end (2) of the gas feeding conduit(1).

2. Process, according to claim 1, characterized in that it includes, prior to step "a", the steps of: positioning an annular seal (20) around the external end (2) of the gas feeding conduit (1); and displacing the tubular body (10) from an inoperative position, in which its first end (11) is separated from the external end (2) of the gas feeding conduit (1), to an operative position in which said first end (11) elastically deforms a portion of the annular seal ring (20) compressing it against the external end (2) of the gas feeding conduit (1).

3. Pressurizing and sealing device for hermetic systems, provided with a gas feeding conduit (1) having an open external end (2), characterized in that it comprises:

a tubular body (10) defining an internal chamber (13) between a first end (11), which can be tightly seated against the external end (2) of the gas feeding conduit (1), and a second open end (12), and a pressurized gas inlet nozzle (14) opened into the internal chamber (13);

an elastomeric plug (30) which can be positioned inside the tubular body (10) in a way that it can be selectively displaced from a pressurizing condition, tightly closing the second end (12) of the tubular body (10) when the internal chamber (13) and the hermetic system are pressurized through the pressurized gas inlet nozzle (14), to a plugging condition in which it is sealingly fitted and retained in the external end (2) of the gas feeding conduit (1) after said pressurizing has ended; and an impelling means (40) coupled to the tubular body (10) and selectively activated through the second end (12) of the latter such that it conducts the elastomeric plug (30) from the pressurizing condition to the plugging condition.

4. Device, according to claim 3, characterized in that it comprises an annular seal (20) which can be positioned around the external end (2) of the gas feeding conduit (1) and which can be elastically deformed to an operative condition, compressing the external end (2) so as to provide the tight seating of the first end (11) on the external end (2) of the gas feeding conduit (1).

5. Device, according to claim 4, characterized in that the tubular body (10) can be selectively displaced between an inoperative position, in which its first end (11) is separated from the external end (2) of the gas feeding conduit (1), and an operative position, in which said first end (11) elastically deforms a portion of the annular seal (20) to the operative condition in which it compresses the external end (2) of the gas feeding conduit (1).

6. Device, according to claim 5, characterized in that it comprises a positioning element (50) carrying the annular seal (20) and which can be selectively displaced between an inoperative position, in which the annular seal (20) is separated from the external end (2) of the gas feeding conduit (1), and an operative position in which said annular seal (20) is positioned around said external end (2).

7. Device, according to claim 6, characterized in that the positioning element (50, defines an external guide for displacing the tubular body (10) between its inoperative and operative positions, and in that, in its inoperative position, the first end of the tubular body (10) is separated from the annular seal (20).

8. Device, according to claim 7, characterized in that the operative position of the tubular body (10) is maintained by a compressing element (60) which acts against said tubular body (10).

9. Device, according to claim 6, characterized in that the compressing element (60) is provided between the second end (12) of the tubular body (10) and said positioning element (50).

10. Device, according to claim 9, characterized in that the inoperative position of the tubular body (10) is maintained against the compressing element (60).

11. Device, according to claim 10, characterized in that the positioning element (50) takes the shape of a tubular cover, inside which the tubular body (10) can be displaced between its inoperative and operative positions.

12. Device, according to claim 11, characterized in that the compressing element (60) is a helicoidal spring positioned inside the tubular cover.

13. Device, according to claim 12, characterized in that the impelling means (40) has the form of an insertion rod located in the tubular body (10) beginning at the second end (12) of the body and having a respective internal end (41) which can be attached to the elastomeric plug (30) to conduct the latter from the pressurizing condition to the plugging condition.

* * * * *